(12) United States Patent
Shin et al.

(10) Patent No.: US 7,781,644 B2
(45) Date of Patent: Aug. 24, 2010

(54) **ARABIDOSIS *ATLEJ1* GENE INVOLVED IN INHIBITING BIOSYNTHESIS OF JASMONIC ACID AND ETHYLENE AND METHOD FOR PRODUCING MALE-STERILE PLANT USING THE SAME**

(75) Inventors: Jeong Sheop Shin, Seoul (KR); Kwang Wook Jung, Seoul (KR); Kyoung Shin Yoo, Seoul (KR); Mei Hua Cui, Seoul (KR); Yun Young Kim, Seoul (KR); Sung Han Ok, Seoul (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 600 days.

(21) Appl. No.: 11/695,841

(22) Filed: Apr. 3, 2007

(65) Prior Publication Data

US 2008/0120735 A1  May 22, 2008

(30) Foreign Application Priority Data

Jul. 14, 2006  (KR) ............ 10-2006-0066605

(51) Int. Cl.
*C12N 15/82* (2006.01)
*C07H 21/04* (2006.01)

(52) U.S. Cl. ............ 800/278; 800/283; 536/23.6
(58) Field of Classification Search ............ None
See application file for complete search history.

(56) References Cited

U.S. PATENT DOCUMENTS

| 6,207,883 | B1 | 3/2001 | Baudot et al. |
| 6,476,297 | B1 | 11/2002 | Mascarehas et al. |
| 6,740,748 | B1 | 5/2004 | Know et al. |
| 7,141,424 | B2 | 11/2006 | Shin et al. |
| 7,193,076 | B2 * | 3/2007 | Shin et al. ............ 536/24.1 |

FOREIGN PATENT DOCUMENTS

| EP | 01528105 A1 | 4/2005 |
| KR | 20030045732 A | 6/2003 |
| KR | 1020060006150 A | 1/2006 |
| WO | 0177333 A1 | 10/2001 |

OTHER PUBLICATIONS

Yamada et al, Database GenEmbl, Sep. 18, 2002.*

* cited by examiner

*Primary Examiner*—Eileen B O Hara
(74) *Attorney, Agent, or Firm*—Sughrue Mion, PLLC

(57) ABSTRACT

Disclosed herein are an *Arabidopsis* gene (AtLEJ1), acting as an inhibitor of the biosynthesis of the phytohormones jasmonic acid and ethylene, and a method for producing a male sterile transgenic plant using the same. The gene guarantees stable male sterile strains which need no maintainers for the maintenance thereof. Also, the transgenic plants comprising the gene can be readily restored to a fertile phenotype merely through hormonal treatment. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

8 Claims, 8 Drawing Sheets
(7 of 8 Drawing Sheet(s) Filed in Color)

FIG. 1

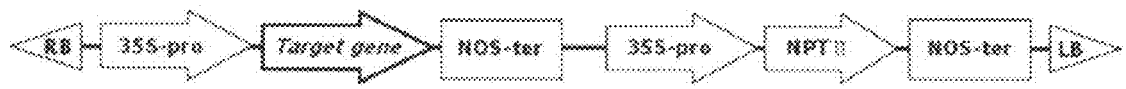

FIG. 2

```
ATGGGTTCAATCTCTTTATCCAATTCTATGCCCATAACTCGACTTCCACTACTT
ACATCACTCTATCATCAAAGCTTCCTTCCGATTTCTTCTTCATCTTTCTCTCTT
CTTCCTCTCTAATCGTCGTCGGTCCTCCACTTTTTCACCGTCAATCACCGTC
TCTGCCTTCTTGGCTGCTCCTGCCAGCGTTAATAATAATAACTCTGTTCCGGCA
AAAAATGGAGGTTACACAGTTGGGGATTTCATGACTCCGAGACAGAATTTCA
CGTTGTTAAGCCCTCTACGTCGGTCGATGATGCCTTGGAACTTCTGGTTGAGAA
GAAAGTCACGGGATTGCCTGTAATTGACGATAATTGGACACTGGTTGGTGTTG
TTTCTGATTACGATTTGCTTGCATTGGACTCCATCTCTGGTCGCAGTCAAAATG
ATACAAACTTGTTCCCTGATGTCGACAGTACCTGGAAAACGTTTAACGAACTAC
AGAAACTGATCAGTAAGACATATGGAAAAGTTGTTGGACACTTGATGACACCG
TCCTCTCGTTGTCCGTGATTCTACCAATTTAGAAGATGCAGCCAGGTTGCTT
CTGGAAACAAAGTTCCGAAGATTACCCGTTGTTGATGCTGATGGAAAACTGAT
TGGGATCCTTACAAGGGGAAACGTTGTAAGGGCTGCGCTGCAGATCAAACGGGA
AACCGAGAACTCTACATAG
```

FIG. 3

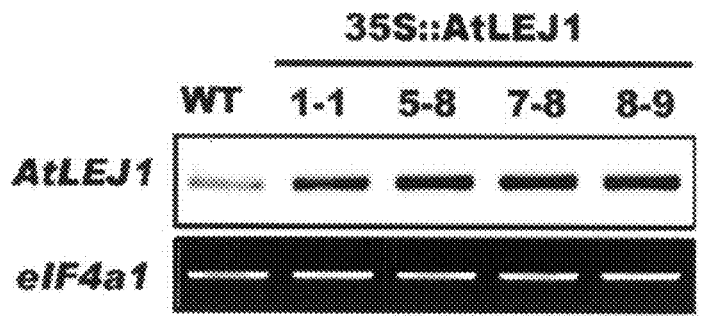

Normal wild-type
(Normal pollination along with anther dehiscence at flowering time)

AtJRJ1-overexpressed plant
(Sterility observed due to defective anther dehiscene)

A, anther; F, filament; Ov, ovary; Sg, stigma ; Sy, style; PG, pollen grain.

Ap, aperture; C, connective; E, epidermis; Ex, exine; F, filament; LW, inner locule wall; Ov, ovary; Sg, stigma; Sy, style; St, stomium; PG, pollen grain.

able ARABIDOSIS *ATLEJ1* GENE INVOLVED IN INHIBITING BIOSYNTHESIS OF JASMONIC ACID AND ETHYLENE AND METHOD FOR PRODUCING MALE-STERILE PLANT USING THE SAME

CROSS-REFERENCE TO RELATED PATENT APPLICATION

This application claims the benefit of Korean Patent Application No. 10-2006-0066605, filed on Jul. 14, 2006, in the Korean Intellectual Property Office, the disclosure of which is incorporated herein in its entirety by reference.

BACKGROUND OF THE INVENTION

1. Technical Field

The present invention relates to an *Arabidopsis* AtLEJ1 gene which functions to inhibit the biosynthesis of the phytohormones jasmonic acid and ethylene. More particularly, the present invention relates to a male sterility-inducing gene that guarantees the security of a stable sterile line and requires no maintainers to maintain male sterility in the line. The present invention is also concerned with a male sterile, transgenic plant comprising the gene, which can be restored to a fertile phenotype by simple hormonal treatment, and to a method for producing the same.

2. Background Art

The development of new plant varieties is very important in view of securing foodstuff or being competitive in the floricultural industry of high-value plants, for example, roses and orchids, and intensive and extensive research on new plant varieties has been done in order to gain a competitive advantage. The development of novel plant varieties is accomplished, for the most part, through hybridization and gene manipulation.

In most cases, F1 hybrids between pure male and female lines are used for new plant varieties because they show heterosis. That is, generally, F1 hybrids outgrow their parents and bear more progeny, show more uniform properties and have shorter flowering and ripening time periods, thus being more tolerant of poor environments than their parents.

It is relatively easy to produce hybrid seeds from plants that have big flowers and many seeds per fruit, such as cucurbitae, because they are susceptible to artificial pollination. However, onions and carrots are difficult to artificially pollinate due to their small flowers. Only a small number of seeds can be obtained in one round of crossing, making it impractical to produce hybrids by artificial pollination. Furthermore, hermaphrodite plants require emasculation, which is labor-intensive, time-consuming work for removing maternal line stamens in flower buds, as a prerequisite to artificial crossing.

If there is a male-sterile line, females thereof may be used along with males from a normal fertile line. In this case, F1 hybrid seeds can be obtained through open pollination without emasculation. Thus, the development of male-sterile plants is very important for the development of new varieties. Male sterility is defined as the failure of plants to produce functional anthers, pollen, or male gametes, which is largely due to malformation of male flowers or anthers or defective anther dehiscence.

Male sterility can be achieved spontaneously or artificially via mutations in nuclear and/or cytoplasmic genes. Genetic mail sterility is expressed mainly as a survival disadvantage and shows a recessive inheritance pattern. Because sterility is obtained only in homozygously recessive alleles, a lot of effort must be made to maintain and proliferate the sterile line. As for plants with small flowers, their fertility is difficult to determine. Further, male sterility is difficult to apply to crops which need a long period of time for flowering.

In the meanwhile, the progeny of cytoplasmic male sterile plants would always be male sterile even if they are interbred with any fertile strain. Thus, the male sterile progeny must be crossed with various fertile strains to find individuals or lines that can produce 50% or 100% sterile strains, that is, maintainer lines. However, this is not practical. Artificial male sterility has been introduced through applying radiation or chemicals to male sterile lines for breeding F1 hybrids. Such radiation- or chemical-induced male sterility is so unstable that it is difficult to put into practice.

In spite of tremendous investment in the research and development of male sterile plants for the production of F1 hybrids, only modest results have been achieved due to the above-mentioned problems with male sterile plants. If the disadvantages with the male sterile plants could be circumvented, that is, if stable male sterile lines could be secured and maintained without other maintainer lines, they would be useful in the development of new varieties and in the industrial production of highly valuable plants.

Therefore, there has been a need for novel genes that allow for the stable male sterile lines without other maintainer lines.

SUMMARY OF THE INVENTION

Accordingly, the present invention has been made keeping in mind the above problems occurring in the prior art, and an object of the present invention is to provide a novel, male sterility-inducing gene which guarantees the security of a stable sterile line and needs no maintainers for the maintenance of male sterility in the line.

Another object of the present invention is to provide a recombinant vector carrying the novel male sterility-inducing gene and a transgenic plant transformed therewith.

A further object of the present invention is to provide a method for producing a male sterile transgenic plant and a method for restoring the male sterile transgenic plant to a fertile phenotype.

Leading to the present invention, intensive and thorough research into male sterility that can be readily restored to fertility, conducted by the present inventors, resulted in the finding that a novel *Arabidopsis* gene AtLEJ1 induces male sterility by inhibiting the biosynthesis of the phytohormones jasmonic acid and ethylene, and the transgenic plant comprising the gene can be readily restored to a fertile phenotype simply by hormonal treatment.

Therefore, in accordance with an aspect of the present invention, there is provided a male sterility-inducing gene (AtLEJ1), derived from *Arabidopsis*, comprising the nucleotide sequence of SEQ ID NO.: 1.

The gene encodes a protein which inhibits the biosynthesis of jasmonic acid or ethylene to induce male sterility.

In accordance with another aspect, the present invention provides a recombinant vector carrying the male sterility-inducing gene and a transgenic plant transformed therewith.

The recombinant vector is a transformation binary vector for use in various plants.

In accordance with a further aspect, the present invention provides a method for restoring a plant in which the gene is expressed into a fertile phenotype, comprising treatment with jasmonic acid or ACC (1-aminocyclopropane-1-carboxylate).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other objects, features and other advantages of the present invention will be more clearly understood from the following detailed description taken in conjunction with the accompanying drawings, in which:

FIG. 1 is a structural view showing left border and right border cassettes of a pCAMBIA2300 vector for cloning the *Arabidopsis* AtLEJ1 gene, involved in inhibiting the biosynthesis of the phytohormones jasmonic acid and ethylene;

FIG. 2 is a cDNA nucleotide sequence of the ORF of the *Arabidopsis* AtLEJ1 gene involved in inhibiting the biosynthesis of the phytohormones jasmonic acid and ethylene (SEQ ID NO: 1);

FIG. 3 shows an expression pattern of the *Arabidopsis* AtLEJ1 gene in a transgenic plant comprising the *Arabidopsis* AtLEJ1 gene;

DETAILED DESCRIPTION OF THE INVENTION

The object, characteristic and advantages of the present invention will be more readily comprehensible with reference to the detailed description and the attached drawings, which explain a preferred embodiment thereof.

The total nucleotide sequence of *Arabidopsis* is already known. Based on the nucleotide sequence, some genes were determined with regard to positions, domains, exons and introns thereof by inference, but the domains and functions of most genes remain unknown.

Of the genes unknown thus far, a putative gene AtLEJ1 (At4g34120) relating to male sterility is selected, cloned to a plant transformation binary vector, and analyzed for nucleotide sequence (SEQ ID NO.: 1) in the present invention (see FIGS. 1 and 2).

Figure 4:
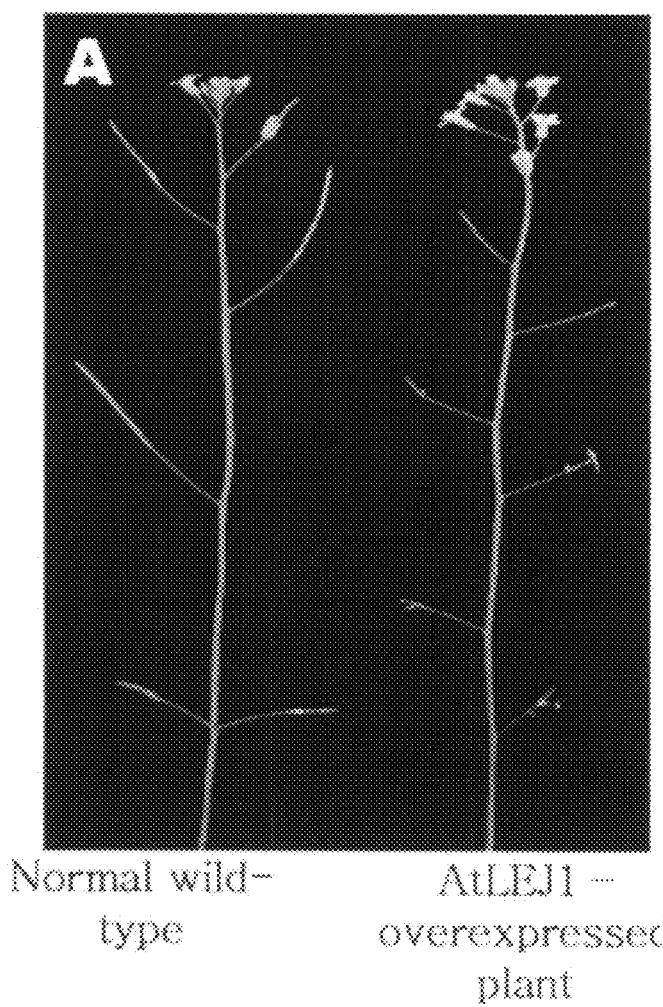
FIGS. 4 and 5 are photographs showing the fertile phenotype of the wild-type and the male-sterile phenotype of the transgenic plant comprising the *Arabidopsis* AtLEJ1 gene, involved in inhibiting the biosynthesis of the phytohormones jasmonic acid and ethylene.
Figure 5:
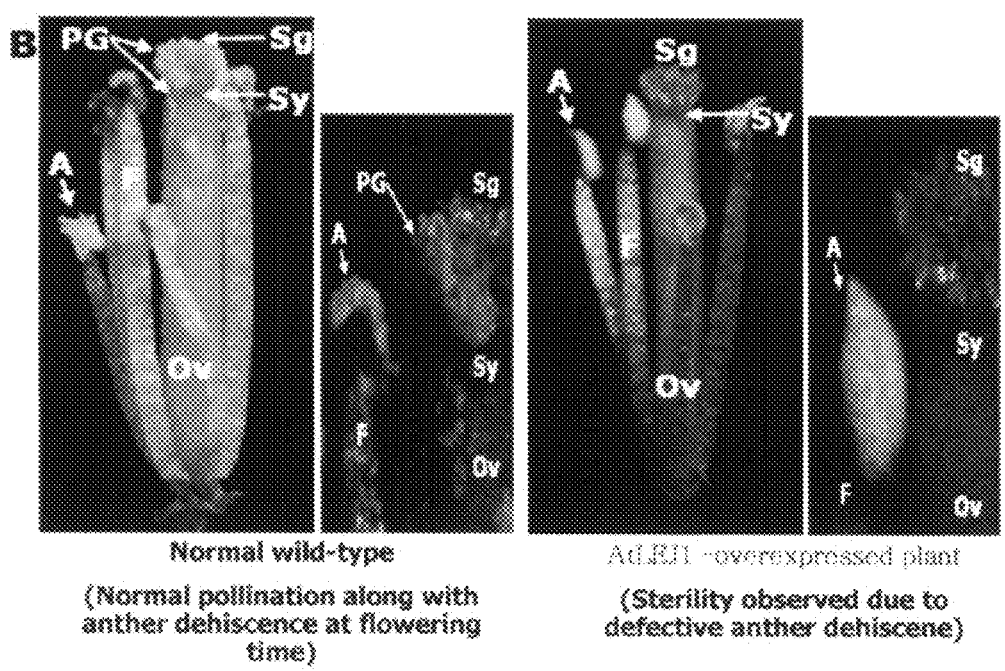

The overexpression of AtLEJ1 gene of the present invention via the recombinant binary vector in *Arabidopsis* is found to result in male sterility due to defective anther dehiscence (FIGS. 3, 4 and 5).

Various techniques well known to those skilled in the art may be used to construct a recombinant vector carrying the gene of the present invention and to introduce the recombinant vector into plants (refer to: Clough S J and Bent A F, 1998. Floral dip: a simplified method for *Agrobacterium*-mediated transformation of *Arabidopsis thaliana*. Plant J 16:735-43). For example, *Agrobacterium*-mediated transformation may be used.

In another aspect, the present invention provides a PCR primer suitable for amplifying the DNA fragment of SEQ ID NO.: 1, said primer being represented by SEQ ID NOS.: 2 and 3 (refer to Table 1).

Figure 6:
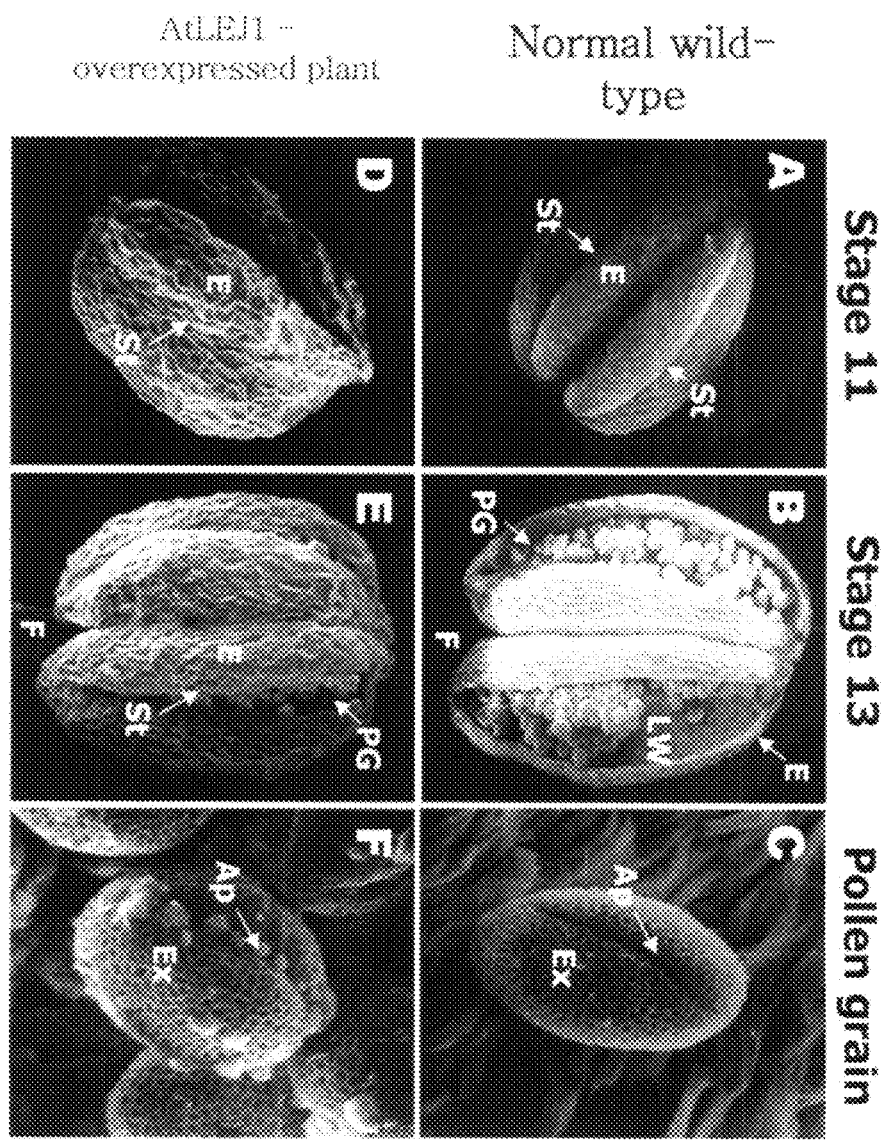
FIG. 6 shows the fertile phenotype of the wild-type and the male-sterile phenotype of the transgenic plant, in which the *Arabidopsis* AtLEJ1 gene, which inhibits the biosynthesis of the phytohormones jasmonic acid and ethylene, is overexpressed, in electron scanning microscope photographs.
Figure 7:
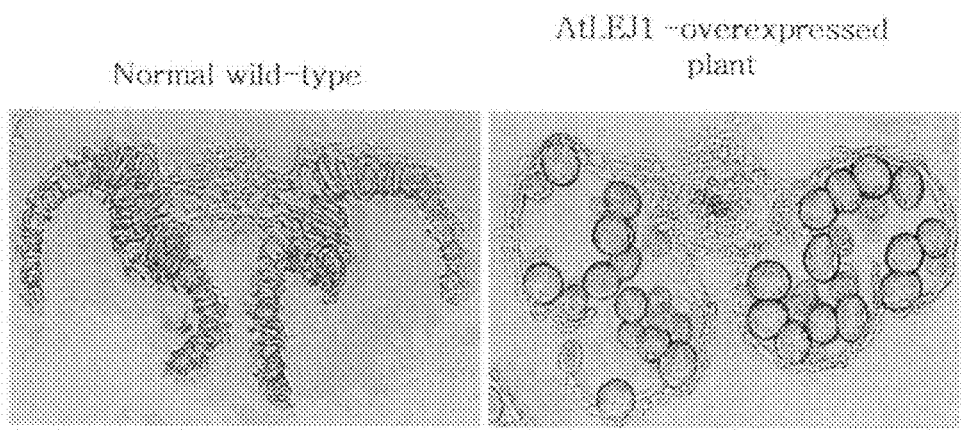
FIG. 7 shows sectioned anther endothecium cells of the wild-type and the transgenic plant, in which the *Arabidopsis* AtLEJ1 gene, which inhibits the biosynthesis of the phytohormones jasmonic acid and ethylene, is overexpressed, after staining for visualizing the lignification thereof.

These plants have normal pollen, but are male sterile because they are defective in the biosynthesis of the phytohormones jasmonic acid and ethylene (FIGS. 6 and 7).

Figure 8:
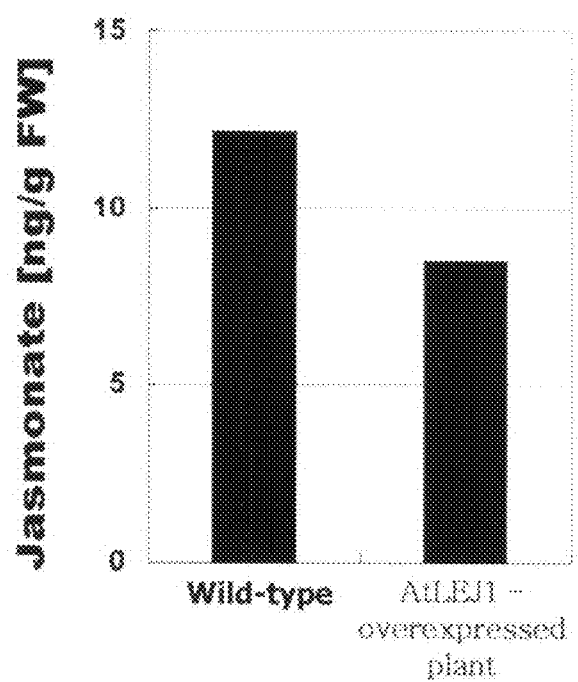
FIG. 8 is a graph showing the levels of total jasmonic acid in flowers of the wild-type and the transgenic plant, in which the *Arabidopsis* AtLEJ1 gene, which inhibits the biosynthesis of the phytohormones jasmonic acid and ethylene, is overexpressed.
Figure 9:
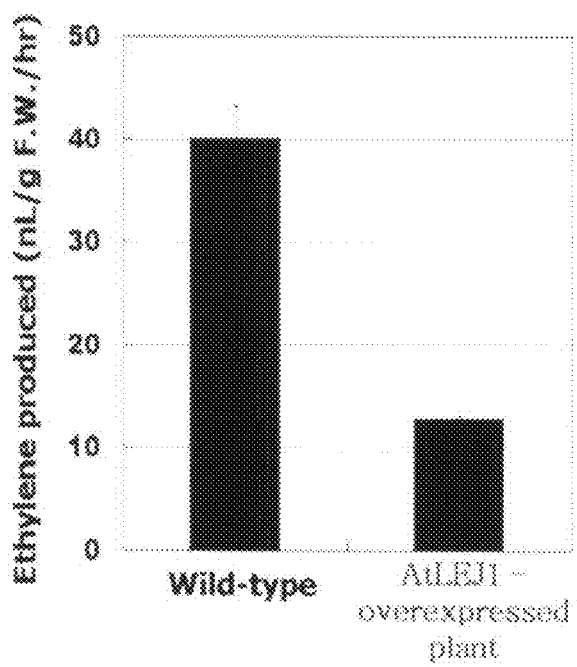
FIG. 9 is a graph showing the levels of total ethylene in flowers of the wild-type and the transgenic plant, in which the *Arabidopsis* AtLEJ1 gene, which inhibits the biosynthesis of the phytohormones jasmonic acid and ethylene, is overexpressed.

Further, the fertility of the plants according to the present invention can be restored through artificial treatment with the two phytohormones rather than other chemicals (refer to FIGS. 8 and 9).

Therefore, the male-sterile plants transformed with the gene of the present invention are stable and need no maintainers. Consequently, the present invention can be effectively applied for the development of new varieties.

A better understanding of the present invention may be obtained through the following examples, which are set forth to illustrate, but are not to be construed as the limit of the present invention.

Example 1

Cloning of Novel Gene AtLEJ1

A set of primers having restriction enzyme site XbaI (for 5' end) and BglII site (for 3' end) (Table 1) was used in PCR for amplifying the ORF (open reading frame) of the gene AtLEJ1 (At4g34120) from a cDNA library constructed from the total RNA of *Arabidopsis* (*Arabidopsis thaliana* ecotype Columbia).

Following digestion with the restriction enzymes, the PCR product was cloned in the plant transformation binary vector pCAMBIA2300, in which a CaMV (Cauline flower mosaic virus) 35S is positioned between a left border and a right border (FIG. 1). Base sequencing was conducted to determine whether the cloning succeeded or failed (FIG. 2).

TABLE 1

5'-CGA-TCT-AGA-ATA-TGG-GTT-CAA-TCT-CTT-TAT-CC  32-mer
(SEQ ID NO.: 2)

5'-TAG-AGA-TCT-CTA-TGT-AGA-GTT-CTC-GGT-TTC-CCG-T  34-mer
(SEQ ID NO.: 3)

Example 2

Induction of Male Sterility by AtLEJ1 Overexpression

The vector prepared in Example 1 was introduced into *Agrobacterium* GV3101 using a Freeze-thaw method (An, G. 1987, Methods in Enzymology). The *Agrobacterium* thus transformed was transfected into *Arabidopsis* using a flower dipping method (Clough and Bent, 1998, The Plant Journal). The transgenic *Arabidopsis* was screened over three generations to obtain a $T_3$ line.

Total RNA was isolated from the transgenic plant and the wild-type and subjected to RT-PCR, which was performed with 27 cycles of denaturation at 95° C. for 20 sec, annealing at 53° C. for 20 sec, and extension at 72° C. for 40 sec, followed by 3 min of final extension at 72° C. These RT-PCR results showed that the AtLEJ1 gene was definitely more highly expressed in the transformed plant than in the wild type. In this regard, eIF4a1 was used as an internal control (FIG. 3).

As apparent from phenotypic comparison with the wild type, showing normal fertility, the AtLEJ1-overexpressed plant was obviously sterile (FIG. 4). Anatomic microscopy showed that the AtLEJ1-overexpressed plant did not release pollen grains upon and after the time point of anther dehiscence (FIG. 5).

For the more detailed observation of the phenotype of stamens, flowers of the wild-type and the AtLEJ1-overexpressed plant were dipped in a fixing solution (4% paraformaldehyde and 2.5% glutaraldehyde in a 0.05 M potassium phosphate buffer) and dehydrated with a series of ethanol solutions (30%, 50%, 70%, 90%, 95%, 100%), followed by a critical point drying process using liquid $CO_2$. The stamens of the flower samples thus obtained were observed under a scanning electron microscope. As shown in FIG. 6, the stamens of the AtLEJ1-overexpressed plant were in a much higher desiccation phase than were those of the wild-type, even in Stage 11, in which anther dehiscence had not taken place. Also, the transgenic plant still remained in the desiccation phase, thus not releasing pollen grains, while the wild-type entered Stage 13, in which anther dehiscence occurred. However, the AtLEJ1-overexpressed plant was observed to have pollen grains of the same normal phenotype as in the wild-type.

In order to examine the developmental process of anthers at the cell level, flowers of the wild-type and the AtLEJ1-overexpressed plant were dipped in a fixing solution, dehydrated with a series of ethanol solutions, and embedded in paraffin (Paraplast), followed by microtome section at 8 μm. The sections were stained with 2% phloroglucinol to visualize the lignification of the endothecium cells, known to play an important role in anther dehiscence, and were washed with 9N HCl. Microscopic observations are shown in FIG. 7. As seen in the microscopic views, the endothecium cells of the wild-type were stained with phloroglucinol (in red), verifying that they underwent normal lignification. However, no red colors were visualized in the stamens of the AtLEJ1-overexpressed plant, indicating that lignification did not progress in the endothecium cells thereof.

Example 3

Measurement of Levels of Jasmonic Acid and Ethylene Using Floral Structure of the AtLEJ1-Overexpressed Plant Previous studies reported that the inhibition of jasmonic acid biosynthesis in *Arabidopsis* retarded anther dehiscence, leading to sterility. Although its exact role in the anther dehiscence process of *Arabidopsis* has not been reported, ethylene is known to play an important role in the anther dehiscence of tobacco. On the basis of these previous findings, the flowers of the AtLEJ1-overexpressed plant were analyzed for total jasmonic acid and ethylene levels using gas chromatography (GS/MS). The total jasmonic level of the AtLEJ1-overexpressed plant was found to be 30% lower than that of the wild type, as seen in FIG. 8. The AtLEJ1-overexpressed plant was also decreased in ethylene level by as much as about 70%, compared with the wild-type (FIG. 9). Thus, these data indicate that the gene AtLEJ1 according to the present invention inhibits the biosynthesis of jasmonic acid and ethylene, thus inducing anther dehiscence-defective male sterility.

Example 4

Restoration of Male-Sterile AtLEJ1-Overexpressed Plant to Fertile Phenotype by Artificial Treatment with Jasmonic Acid and an Ethylene Precursor ACC (1-aminocyclopropane-1-carboxylic acid)

In order to examine whether or not the AtLEJ1-overexpressed plant was restored to a fertile phenotype upon artificial treatment with external jasmonic acid or ACC (1-aminocyclopropane-1-carboxylate, an ethylene precursor), the following experiment was conducted.

First, a flower bud cluster of the AtLEJ1-overexpressed plant was treated with 500 μM jasmonic acid. For a negative control, non-treatment or water alone, was provided.

Figure 10:
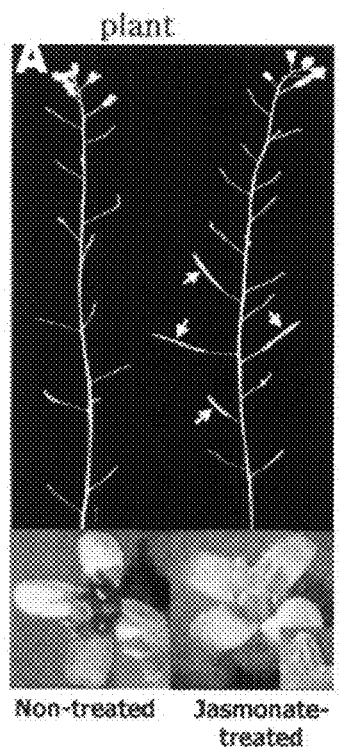
FIGS. 10 and 11 are photographs showing the restoration to a fertile phenotype of the male-sterile plant in which the *Arabidopsis* AtLEJ1 gene, which inhibits the biosynthesis of the phytohormones jasmonic acid and ethylene, is overexpressed, by treatment with jasmonic acid.
Figure 11:
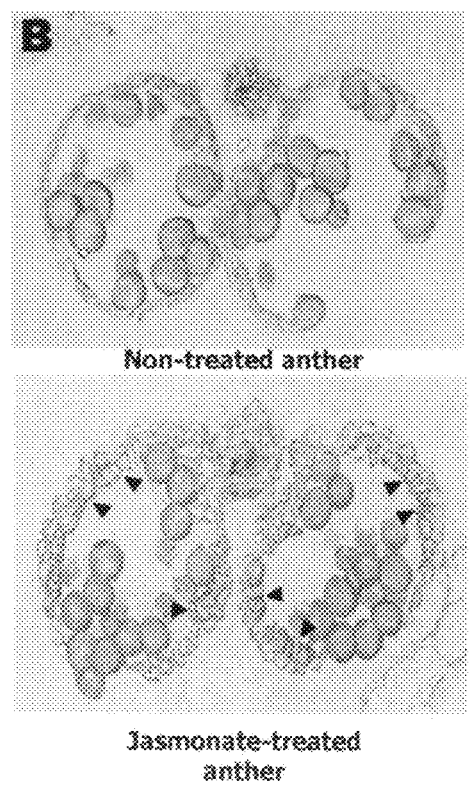

As seen in FIG. 10, the plant was, at least partly, restored to a fertile phenotype one week after treatment with jasmonic acid (white arrows) while the control remained sterile. The jasmonic acid-treated flowers on day 2 were microscopically observed to enter anther dehiscence. The flowers obtained day 2 after treatment with jasmonic acid were embedded in paraffin (Paraplast) and then stained with phloroglucinol for microscopic observation. As seen in FIG. 11, the endothecium cells of stamens were lignified (dark arrows) to anther dehiscence, so that the pollen grains were normally released.

Figure 12:
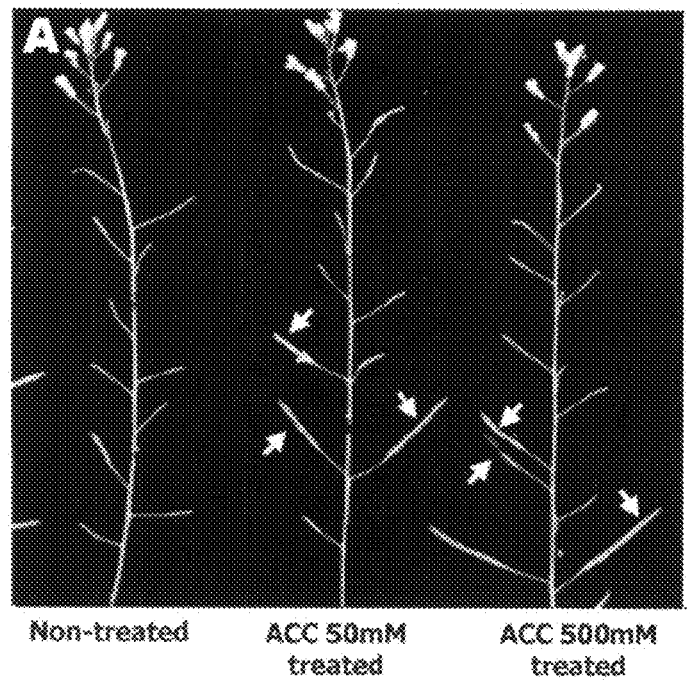
FIGS. 12 and 13 are photographs showing the restoration to a fertile phenotype of the male-sterile plant in which the *Arabidopsis* AtLEJ1 gene, which inhibits the biosynthesis of the phytohormones jasmonic acid and ethylene, is overexpressed, by treatment with ACC.
Figure 13:
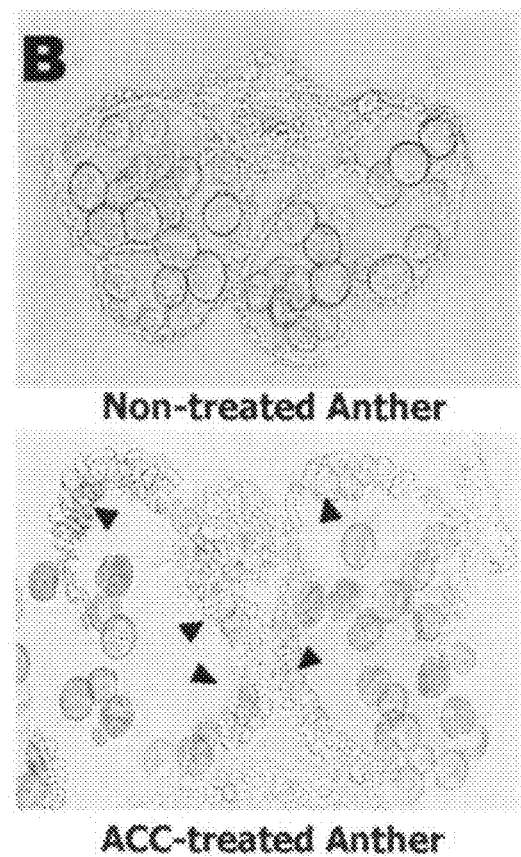

Likewise, the male-sterile AtLEJ1-overexpressed plant was restored to a fertile phenotype upon treatment with 50 mM or 500 mM of the ethylene precursor ACC (FIG. 12). Lignification was also found in the endothecium cells of stamens of the treated plant (FIG. 13).

INDUSTRIAL APPLICABILITY

As described hitherto, the AtLEJ1 gene of the present invention induces male sterility in plants, and the male-sterile transgenic plant having the gene is stable and can be maintained without a maintainer. In addition, the male-sterile transgenic plant can be readily restored to a fertile phenotype by hormonal treatment. Therefore, the present invention is very useful in the development of new plant varieties and in the industrial production of highly valuable plants.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A transgenic plant, transformed with a gene comprising a male sterility-inducing gene (AtLEJ1), said gene comprising the nucleotide sequence of SEQ ID NO: 1.

2. A transgenic plant, transformed with a recombinant vector which carries a male sterility-inducing gene (AtLEJ1), said gene comprising the nucleotide sequence of SEQ ID NO: 1.

3. The transgenic plant according to claim 1 or claim 2, wherein the transgenic plant is restored to a fertile phenotype upon treatment with jasmonic acid or 1-aminocyclopropane-1-carboxylate).

4. A method for restoring fertility to a plant in which a male sterility-inducing gene (AtLEJ1) of claim 1 is overexpressed, the method comprising treating the plant with jasmonic acid or 1-aminocyclopropane-1-carboxylate, wherein the gene (AtLEJ1) comprises the nucleotide sequence of SEQ ID NO: 1.

5. A method for producing a plant with male sterility, comprising over-expressing a male sterility-inducing gene (AtLEJ1) derived from *Arabidopsis*, in the plant, wherein the gene (AtLEJ1) comprises the nucleotide sequence of SEQ ID NO: 1.

6. A method according to claim 5, wherein the gene (AtLEJ1) encodes a protein which inhibits biosynthesis of jasmonic acid or ethylene to induce male sterility.

7. A method according to claim 5, which comprises introducing a recombinant vector into the plant, wherein the recombinant vector carries the gene (AtLEJ1) consisting of the nucleotide sequence of SEQ ID NO: 1.

8. A method according to claim 5, wherein the gene (AtLEJ1) is amplified by PCR with a primer of SEQ ID NOS: 2 or 3.

* * * * *

SEQUENCE LISTING

<160> NUMBER OF SEQ ID NOS: 3

<210> SEQ ID NO 1
<211> LENGTH: 717
<212> TYPE: DNA
<213> ORGANISM: Arabidopsis thaliana

<400> SEQUENCE: 1

```
atgggttcaa tctctttatc caattctatg cccataactc gacttccact acttacatca      60
ctctatcatc aaagcttcct tccgatttct tcttcatctt tctctcttct tcctctctct     120
aatcgtcgtc gctcctccac tttttcaccg tcaatcaccg tctctgcctt cttcgctgct     180
cctgccagcg ttaataataa taactctgtt ccggcaaaaa atggaggtta cacagttggg     240
gatttcatga ctccgagaca gaatttgcac gttgttaagc cctctacgtc ggtcgatgat     300
gcgttggaac ttctggttga gaagaaagtc acgggattgc ctgtaattga cgataattgg     360
acactggttg gtgttgtttc tgattacgat ttgcttgcat tggactccat ctctggtcgc     420
agtcaaaatg atacaaactt gttccctgat gtcgacagta cctggaaaac gtttaacgaa     480
ctacagaaac tgatcagtaa gacatatgga aaagttgttg gagacttgat gacaccgtct     540
cctctcgttg tccgtgattc taccaattta gaagatgcag ccaggttgct tctggaaaca     600
aagttccgaa gattacccgt tgttgatgct gatggaaaac tgattgggat ccttacaagg     660
ggaaacgttg taagggctgc gctgcagatc aaacgggaaa ccgagaactc tacatag       717
```

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
cgatctagaa tatgggttca atctctttat cc                                    32
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
tagagatctc tatgtagagt tctcggtttc ccgt                                  34
```